(12) United States Patent
Johnson et al.

(10) Patent No.: US 7,585,554 B2
(45) Date of Patent: Sep. 8, 2009

(54) WOUND DRESSING, INGREDIENT DELIVERY DEVICE AND IV HOLD-DOWN INCORPORATING A STATICALLY RETAINED HANDLE

(75) Inventors: David R. Johnson, Ada, MI (US); Steven R. Klemm, Grand Rapids, MI (US)

(73) Assignee: Corium International, Inc., Menlo Park, CA (US)

( * ) Notice: Subject to any disclaimer, the term of this patent is extended or adjusted under 35 U.S.C. 154(b) by 715 days.

(21) Appl. No.: 11/173,681

(22) Filed: Jul. 1, 2005

(65) Prior Publication Data

US 2006/0003133 A1 Jan. 5, 2006

Related U.S. Application Data

(60) Provisional application No. 60/585,413, filed on Jul. 2, 2004.

(51) Int. Cl.
*B32B 7/10* (2006.01)
(52) U.S. Cl. .................... 428/40.1; 428/42.2; 428/43.3; 602/57; 602/52; 602/58; 602/41; 128/898
(58) Field of Classification Search ........................ None
See application file for complete search history.

(56) References Cited

U.S. PATENT DOCUMENTS

| | | | |
|---|---|---|---|
| 4,372,303 A | 2/1983 | Grossmann et al. | |
| 4,485,809 A | 12/1984 | Dellas | |
| 4,598,004 A | 7/1986 | Heinecke | |
| 4,600,001 A | 7/1986 | Gilman | |
| 4,614,183 A | 9/1986 | McCracken et al. | |
| 4,753,232 A | 6/1988 | Ward | |
| 4,787,380 A | 11/1988 | Scott | |
| 4,861,665 A | * 8/1989 | Kasahara | ................. 428/411.1 |
| 4,875,473 A | 10/1989 | Alvarez | |
| 4,884,563 A | 12/1989 | Sessions | |
| 4,915,228 A | 4/1990 | Johns | |
| 4,917,112 A | 4/1990 | Kalt | |
| 4,917,929 A | 4/1990 | Heinecke | |
| RE33,353 E | 9/1990 | Heinecke | |
| 4,963,045 A | 10/1990 | Willcox | |
| 5,000,172 A | 3/1991 | Ward | |
| RE33,727 E | 10/1991 | Sims | |
| 5,088,483 A | 2/1992 | Heinecke | |
| 5,160,315 A | 11/1992 | Heinecke et al. | |
| 5,336,162 A | 8/1994 | Ota et al. | |
| 5,413,567 A | 5/1995 | Barth et al. | |
| 5,437,622 A | 8/1995 | Carion | |

(Continued)

OTHER PUBLICATIONS

Exhibit A—a prior art wound dressing device that was publically disclosed and/or offered for sale at least as early as Jul. 1, 2003.

*Primary Examiner*—Jennifer McNeil
*Assistant Examiner*—Vera Katz
(74) *Attorney, Agent, or Firm*—Price, Heneveld, Cooper, DeWitt & Litton, LLP

(57) ABSTRACT

Adhesive devices used as wound dressings, ingredient delivery devices and IV hold-downs include a handling layer comprised of a layer of conductive material and at least one layer of non-conductive material, adhered to the non-adhesive coated side of an adhesive coated polymeric film layer, by an electrostatic charge, rather than by an adhesive.

18 Claims, 2 Drawing Sheets

U.S. PATENT DOCUMENTS

| | | |
|---|---|---|
| 5,520,629 A | 5/1996 | Heinecke et al. |
| 5,531,855 A | 7/1996 | Heinecke et al. |
| 5,599,289 A | 2/1997 | Castellana |
| 5,722,943 A | 3/1998 | Sessions |
| 5,738,642 A | 4/1998 | Heinecke et al. |
| 5,749,842 A | 5/1998 | Cheong et al. |
| 5,931,800 A | 8/1999 | Rasmussen et al. |
| 5,951,505 A | 9/1999 | Gilman et al. |
| 5,994,613 A | 11/1999 | Cummings et al. |
| 6,008,429 A | 12/1999 | Ritger |
| 6,014,585 A * | 1/2000 | Stoddard ................ 607/2 |
| 6,043,406 A | 3/2000 | Sessions et al. |
| 6,096,942 A | 8/2000 | Hack |
| 6,121,508 A * | 9/2000 | Bischof et al. ............ 602/52 |
| 6,225,521 B1 | 5/2001 | Gueret |
| 6,252,129 B1 | 6/2001 | Coffee |
| 6,346,653 B1 | 2/2002 | Sessions et al. |
| 2002/0107466 A1 | 8/2002 | Faasse, Jr. |

* cited by examiner

WOUND DRESSING, INGREDIENT DELIVERY DEVICE AND IV HOLD-DOWN INCORPORATING A STATICALLY RETAINED HANDLE

CROSS-REFERENCE TO RELATED APPLICATIONS

This application claims the benefit of U.S. Provisional Application No. 60/585,413, filed on Jul. 2, 2004, the entire contents of which are hereby incorporated by reference.

BACKGROUND OF THE INVENTION

The present invention relates to adhesive devices used as wound dressings, ingredient delivery devices and IV hold-downs.

Prior art wound dressings and IV hold-downs in particular, comprise a layer of polymeric film having an adhesive layer on one side thereof, which is protected during storage and handling by a release liner. U.S. Pat. No. 7,094,944, issued Aug. 22, 2006 discloses such devices which also have a handling member adhered to the non-adhesive coated side of the polymeric film by means of a pressure sensitive adhesive. The pressure sensitive adhesive used between the handle and the polymeric film is less aggressive than the pressure sensitive adhesive used on the underside of the polymeric film, such that, in theory, once the polymeric film is applied to a patient's skin or mucosa, the handle can be peeled away without peeling the polymeric film away from the patient's skin.

In some prior art, such as U.S. Pat. No. 6,096,942, it has been suggested that the handle member can be adhered to the polymeric film member either by low tack adhesive or by electrostatic attraction. There tends to be a natural electrostatic attraction between the two members. See also U.S. Pat. No. 5,437,622 to Carion.

SUMMARY OF THE INVENTION

In the wound dressing, ingredient delivery device and IV hold-down of the present invention, a handle comprising a generally non-conductive layer and a generally conductive layer is adhered to the underlying film of the device by electrostatic charge, rather than by an adhesive. The expense of applying an adhesive layer to the handle member, and the need to balance its adhesion against the adhesion of the adhesive layer on the polymeric film is eliminated.

These and other objects, features and advantages of the invention will be more fully understood and appreciated by reference to the written specification, claims and appended drawings.

DETAILED DESCRIPTION OF PREFERRED EMBODIMENT

Introduction

The term "dressing" as used herein is to be understood to include wound dressings, IV hold-downs and transdermal, dermal, transmucosal and mucosal ingredient delivery systems.

Figure 1:
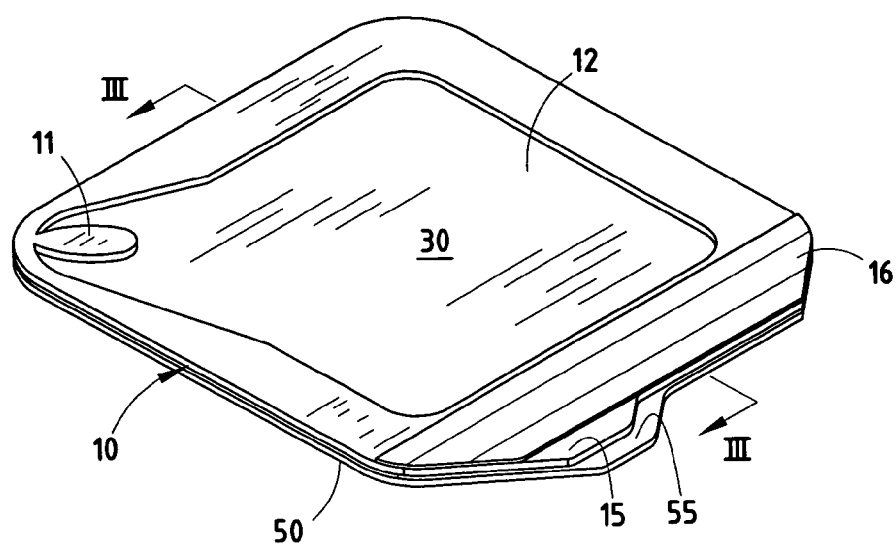
FIG. 1 is a perspective view of the wound dressing, ingredient delivery device, or IV hold-down in accordance with an embodiment of the present invention.
Figure 3:
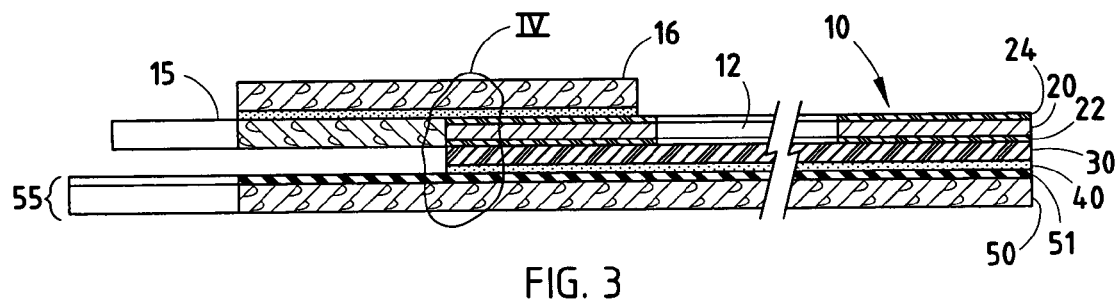
FIG. 3 is a cross-sectional view of the wound dressing, ingredient delivery device, or IV hold-down of FIG. 1, taken along line III-III.
Figure 4:
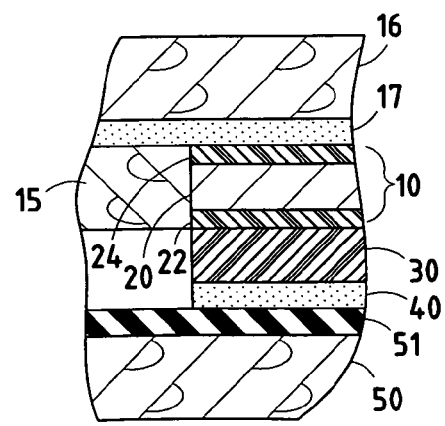
FIG. 4 is an enlarged sectional view (section IV) of the wound dressing, ingredient delivery device, or IV hold-down of FIG. 3.
Figure 2:
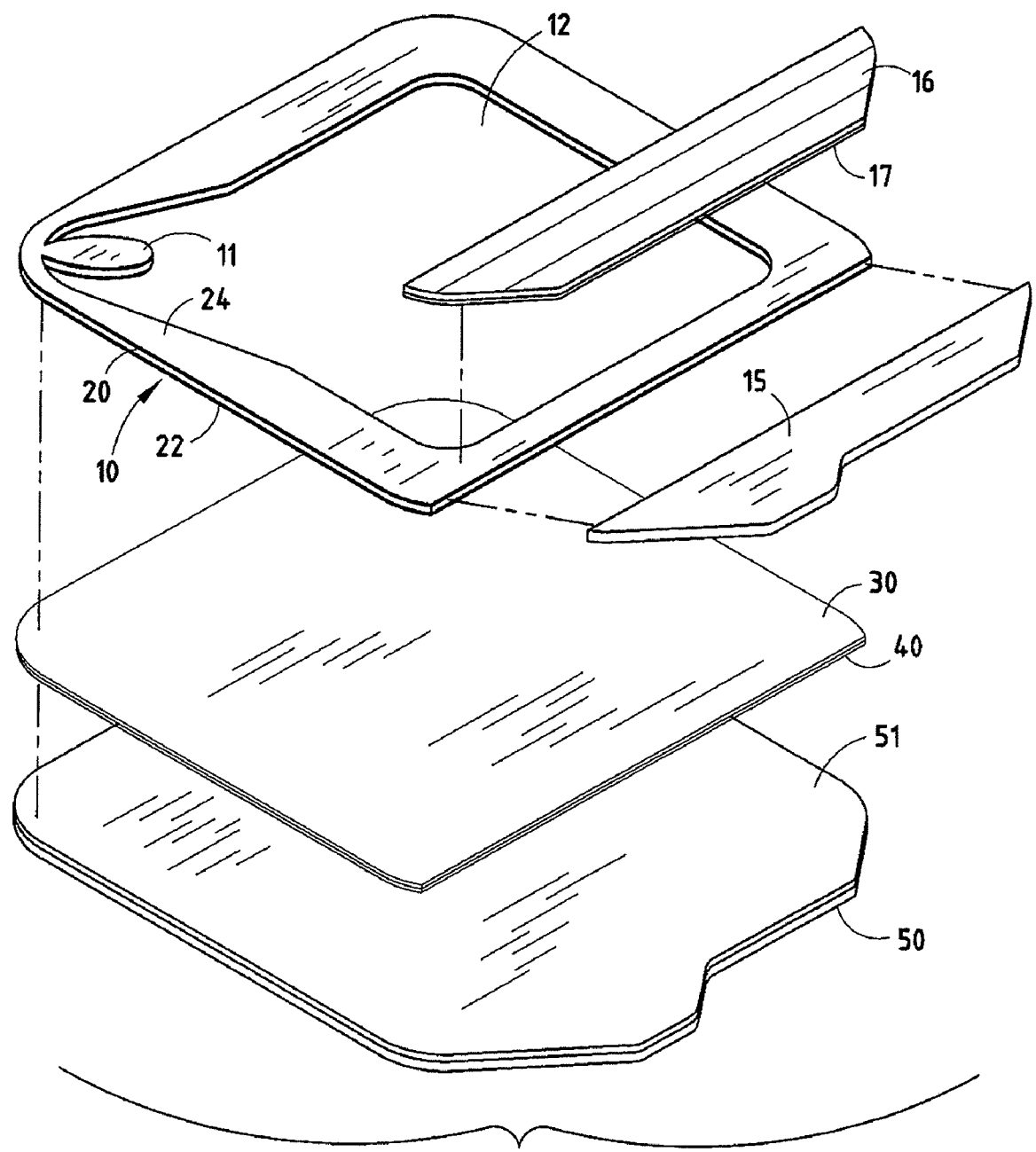
FIG. 2 is an exploded perspective view of the wound dressing, ingredient delivery device, or IV hold-down of FIG. 1.

In the preferred embodiment (FIG. 1), the basic elements of a dressing in accordance with the present invention comprise a handle 10 which is made up of a conductive film 20 affixed to a first polymeric film layer 22 and a second optional polymeric film layer 24, respectively (FIGS. 2-4). Handle 10 is shaped like a window frame, circumscribing a central opening or window 12. Additionally, as depicted in FIG. 2, handle 10 further includes inwardly-projecting first thumb tab 11 disposed within window 12 which is used for the removal of handle 10 from polymeric film layer 30 after the polymeric film has been applied to a patient.

Handle 10 is applied and statically retained to the non-adhesive coated surface of a polymeric film 30 which has a pressure sensitive adhesive layer 40 on the undersurface thereof. Adhesive layer 40 is protected during handling and storage by a release liner 50 having a silicone coating layer 51. Tabs 15 and 55 extend from handle 10 and release liner 50, respectively. In use, release liner 50 is removed from the sub-assembly of polymeric film 30 and handle 10 by grasping tab 15 with the thumb and forefinger of one hand and tab 55 with the thumb and forefinger of the other hand, and separating the two sub-assemblies. Handle 10 is then used to add support to, as well as aid in the application of, polymeric film 30. Once polymeric film 30 has been applied to the patient, the user grasps tab 11 projecting inwardly on handle 10, and peels handle 10 away from the applied polymeric film 30.

Handle 10 is comprised of at least a layer of conductive material 20 affixed to at least a layer of non-conductive material 22 or 24. Optionally, conductive layer 20 may be disposed between two layers of non-conductive polymeric films 22 and 24. However, only one non-conductive layer 22 or 24 is required, and handle 10 can be applied to polymeric film 30 with either conductive layer 20 applied directly against film 30, or with non-conductive layer 22 or 24 lying against film 30. The static change generated during handling of the materials in manufacture is sufficient to electrostatically bond handle 10 to film 30.

An optional corona treatment may be used as a way to increase the electrostatic surface adhesion of the polymeric film. This is accomplished by causing the oxygen molecules within the corona discharge area to break into ions that bond to the surface of the treated material. It is these ions that are extremely receptive to bonding with other materials. This receptiveness or attraction to other materials is what is used to initially bond handle 10 to polymeric film 30 without the use of an adhesive. This static bond, with or without the use of a corona discharge, is sufficient to retain handle 10 to polymeric film 30 during manufacturing, transportation and application.

In addition, a second electrostatic charge is created during the application process which enhances the electrostatic bond between handle 10 to polymeric film 30. This second electrostatic charge is generated when release liner 50 is peeled away from the adhesive layer 40 on the undersurface of film 30. Though not wishing to be bound by theory, when these two materials are separated, a positive charge will accumulate on the surface of the polyurethane and a negative charge on the release liner. Since two oppositely charged surfaces will attract each other, the positive static charge of polymeric film 30 is then attracted to the electron rich, negatively charged, conductive material 20 within handle 10. Therefore, this additional statically attractive force adds to the retention of handle 10 to polymeric film 30, and tends to remain until the user applies the system to the patient, at which time the system is grounded, thereby removing or at least diminishing the electrostatic attractive force.

Handle 10 is preferably made of a stiffer and generally thicker material than that of polymeric film 30 (discussed below). Typical materials for polymeric film layer 22 and optional polymeric film layer 24 are plastic materials which include polyesters, polycarbonates, PVC's, polyurethanes, polyethylene vinyl acetates, polyester copolymers, polyethylenes, and polypropylenes or any other corona treated film which is electrically non-conductive. In the preferred embodiment, conductive layer 20 comprises a layer of aluminum formed and affixed to at least one layer of non-conductive material (i.e. polymeric film layer, etc.). The aluminum is preferably deposited in vaporized form onto the non-conductive material layer during fabrication. Other conductive materials could be used for layer 20. However, this is only the preferred embodiment and other materials, configurations and/or procedures may be used.

Various configurations of the materials that comprise handle 10 are possible. For example, handle 10 may include conductive layer 20 sandwiched between two layers of non-conductive material. Alternatively, conductive layer 20 may be affixed to one layer of non-conductive material, wherein either the conductive layer or the non-conductive layer of handle 10 may be applied to and statically retained to the non-adhesive coated surface of polymeric film 30 which has a pressure sensitive adhesive layer 40 on the undersurface thereof. This configuration is most typically preferred.

A second thumb tab 15 is adhered to handle 10 by tape 16. Second tab 15 is also preferably made of stiffer and generally thicker materials than that of polymeric film 30. Typical of such materials are plastic or paper material. Useable plastics include polyesters, polycarbonates, PVC's, polyurethanes, polyethylene vinyl acetates, polyester copolymers, polyethylenes, and polypropylenes. In the preferred embodiment, a paper material is used. Tab 15 is affixed to and extends beyond handle 10 allowing a user to fold back an end portion of release liner 50 to expose the underside of tab portion 15 wherein the exposed portion can then be used to peel film 30 away from release liner 50.

The tab portion 15 is adhered to handle 10 by tape 16 with adhesive 17 on the underside thereof. Tape 16 is generally formulated to permanently or at least strongly adhere tab 15 to handle 10. In the preferred embodiment a non-woven paper tape using acrylic adhesive is used. However, any type of tape material and/or adhesives which are suitable for this purpose may be used.

Polymeric film 30 is preferably comprised of any breathable and waterproof material. In the preferred embodiment, a polymeric film on the order of from about 0.5 to about 4 mils (0.0005 to 0.004 inches) is preferred. The film is preferably very flexible, allowing it to conform readily to the patient's skin or mucosa. The film must have sufficient strength to afford resistance to damage in handling and in use. It also preferably allows the passage of oxygen, thereby allowing the skin or mucosa to breathe. The polymeric film material preferably is a polyurethane film such as a polyether block amide Pebax® film (MediFilm® 810, 2 mils, Mylan® Mylan Technologies, Inc.). Additionally, copolymers of polyethylene and vinyl acetate are also preferable.

The adhesive layer 40 may be any adhesive that bonds well to skin or mucosa. Preferably, a pressure sensitive adhesive is used. A type of adhesive found useful for adhesive layer 40 is a permanent acrylate-based pressure sensitive adhesive designed for skin, with a peel adhesion level of approximately 50 ounces. Other useful adhesives include, but are not limited to, silicone, urethane, synthetic rubber and natural rubber. Such adhesives can be formulated to adhere releasably to the silicone coated surface 51 of release liner 50. At the same time, they can be formulated to adhere firmly to the patient's skin or mucosa such that polymeric film 30 will not peel away unless someone intends to do so. For example, one can use an acrylate derivative adhesive such as copolymers of alkyl acrylate/vinyl acetate containing —OH or/and —COOH functional groups, or hydrophobic styrenic rubber polymer or PIB containing 1 to 20% hydro-attractants such as PVP, PVA, and cellulose derivatives such as Duro-Tak® acrylate-vinylacetate self-curing pressure sensitive adhesive 87-2516 (National Starch), and PIB containing 20% Kollidon® CL-M polyvinylpolypyrrolidone(BASF).

The entire assembly of handle 10, polymeric film 30 and adhesive layer 40 is releasably adhered to release liner 50. Release liner 50 may be comprised of any material that will releasably adhere adhesive layer 40. However, in the preferred embodiment, release liner 50 is a paper material with a silicone coating 51 on the top surface thereof.

By utilizing a handle member which is comprised of a layer of conductive material 20 affixed to at least one layer of non-conductive material (i.e. polymeric film), an initial static bond is created which is sufficient to retain the handle to the polymeric film 30. Further, a second electrostatic charge is created during the application process which is utilized to create an even stronger electrostatic bond. The present inventive concept utilizes this electrostatic force to retain the handle, thereby eliminating the expense of applying an adhesive layer to the handle and the need to balance its adhesion against the adhesion of the adhesive layer on the polymeric film.

While the embodiments described above are wound dressings or IV hold-down devices, the various aspects of the present invention are also applicable to devices designed to deliver active ingredients to or through the dermal or mucosal layers. Such delivery systems typically deliver the active ingredients via a gel modulated system, membrane modulated system, or an adhesive modulated system.

Of course it is understood that the foregoing are preferred embodiments and changes and variations can be made without departing from the spirit and broader aspects of the invention, as defined in any appended claims, which are to be interpreted in accordance with the principles of patent law, including the Doctrine of Equivalents.

The invention claimed is:

1. A wound dressing/ingredient delivery device/IV hold-down comprising:
    a layer of polymeric film which is adhesively coated on a first side to facilitate adhesion to a patient;
    a handling member comprising at least a layer of conductive material and at least one layer of non-conductive material fixed to the layer of conductive material; and wherein
    the handling member is electrostatically adhered to a second side of the polymeric film, opposite from the adhesive coated side, without an adhesive.

2. The device of claim 1, wherein the conductive material comprises a conductive film.

3. The device of claim 2, wherein the handling member comprises the conductive film sandwiched between a first and a second non-conductive layer.

4. The device of claim 2, wherein the non-conductive material of the handling member is adjacent to and electrostatically interacts with the second side of the polymeric film.

5. The device of claim 1, wherein the polymeric film defines a perimeter edge and the handling member further comprises a first tab member extending away from a portion of the perimeter edge.

6. The device of claim 5, wherein the first tab member is abuttingly disposed against a first end of the layer of conductive material and the layer of conductive material and the layer of nonconductive material of the handling member.

7. The device of claim 6, wherein the first tab member is abuttingly affixed to the handling member with an adhesively backed tape.

8. The device of claim 5, further including:
a release liner having a first side, wherein the first side of the release liner is adhered to the first side of the polymeric film.

9. The device of claim 8, wherein the release liner is made from a paper product and the first side of the release liner is coated with a silicone.

10. The device of claim 8, wherein the release liner further includes:
a second tab portion which overlaps the first tab portion of the handling member.

11. The device of claim 1, wherein the handling member includes an enlarged central opening.

12. The device of claim 1, wherein the layer of polymeric film is adhesively coated with a pressure sensitive adhesive.

13. A wound dressing/ingredient delivery device/IV hold-down comprising:
a polymeric film defining a perimeter and having an adhesive coating on a first side for adhering to a patient;
a handle member releasably adhered to a second side of the polymeric film, opposite from the first side, to facilitate handling of the polymeric film as it is applied to a patient, wherein the handle member includes a handle tab projecting therefrom beyond a portion of the perimeter of the polymeric film;
a release liner, releasably adhered to the adhesively coated first side of the polymeric film, wherein the release liner includes a release tab projecting therefrom beyond a portion of the perimeter of the polymeric film and wherein the handle tab generally overlies the release liner tab, and the release liner tab projects further than the handle tab, and wherein substantially no adhesive is disposed between the handle tab and the release liner tab in the area where the handle tab overlies the release liner tab, whereby in use, the release liner can be removed by grasping the handle tab and the release liner tab and peeling the release liner away from the assembly of the polymeric film and the handle member; and wherein
the handling member comprises at least a layer of conductive material affixed to a layer of non-conductive material, the handling member adhered to the second side of the polymeric film by an electrostatic interaction, rather than by an adhesive.

14. The device of claim 13, wherein the conductive material comprises a conductive film.

15. The device of claim 14, wherein the layer of non-conductive material comprises a first layer of non-conductive material; and including:
a second layer of non-conductive material; and wherein
the handle member comprises the conductive film sandwiched between the first and the second layers of non-conductive material.

16. The device of claim 14, wherein the non-conductive material of the handle member is adjacent to and electrostatically interacts with the second side of the polymeric film.

17. The device of claim 13, wherein the handle tab is abuttingly affixed to a first end of the conductive film and the layer of non-conductive material of the handle member with an adhesively backed tape.

18. A device suitable for use as a wound dressing, ingredient delivery or IV hold-down, comprising:
a handle comprising a thin flexible layer of conductive material defining first and second sides and having a centrally located opening therethrough such that the handle defines a perimeter frame-like member, the handle further comprising a layer of non-conductive material fixed to a selected one of the first and second sides of the layer of conductive material;
a layer of polymeric film having an adhesive coating on a first side of the layer of polymeric film to adhere the layer of polymeric film to a patient;
a releasable liner layer covering the first side of the layer of polymeric film to facilitate handling of the device prior to use; and wherein:
the layer of polymeric film has a second side that is electrostatically adhered to the handle without adhesive.

* * * * *